United States Patent [19]

Scarampi

[11] Patent Number: 4,931,865

[45] Date of Patent: Jun. 5, 1990

[54] APPARATUS AND METHODS FOR MONITORING TELEVISION VIEWERS

[76] Inventor: Sebastiano Scarampi, 25550 Moody Rd., Los Altos Hills, Calif. 94022

[21] Appl. No.: 235,927

[22] Filed: Aug. 24, 1988

[51] Int. Cl.⁵ .......................... H04H 9/00; G06K 9/00
[52] U.S. Cl. ......................................... 358/84; 455/2; 382/2
[58] Field of Search ................ 358/84; 379/92; 455/2; 351/209, 210; 382/2

[56] References Cited

U.S. PATENT DOCUMENTS

| | | | |
|---|---|---|---|
| 3,379,885 | 4/1968 | Nork | 250/83.3 |
| 3,507,988 | 4/1970 | Holmes | 178/6.8 |
| 3,712,716 | 1/1973 | Cornsweet et al. | 351/7 |
| 3,986,030 | 10/1976 | Teltscher | 250/349 |
| 4,034,401 | 7/1977 | Mann | 358/93 |
| 4,075,657 | 2/1978 | Weinblatt | 358/93 |
| 4,146,311 | 3/1979 | Murr | 351/24 |
| 4,582,403 | 4/1986 | Weinblatt | 351/210 |
| 4,599,644 | 7/1986 | Fischer | 358/84 |
| 4,623,230 | 11/1986 | Weinblatt | 351/210 |
| 4,626,904 | 12/1986 | Lurie | 358/84 |
| 4,641,349 | 2/1987 | Flom et al. | 382/2 |
| 4,644,509 | 2/1987 | Kiewit et al. | 367/87 |
| 4,646,145 | 2/1987 | Percy et al. | 358/84 |
| 4,652,915 | 3/1987 | Heller | 358/84 |
| 4,658,290 | 4/1987 | McKenna et al. | 358/84 |
| 4,695,879 | 9/1987 | Weinblatt | 358/84 |
| 4,755,045 | 7/1988 | Borah et al. | 351/210 |
| 4,769,697 | 9/1988 | Gilley et al. | 358/84 |
| 4,779,198 | 10/1988 | Lurie | 358/84 X |
| 4,789,235 | 12/1988 | Borah et al. | 351/210 |
| 4,792,864 | 12/1988 | Watanabe et al. | 358/84 X |
| 4,798,214 | 1/1989 | Haas | 351/210 X |
| 4,858,000 | 8/1989 | Lu | 358/84 |

FOREIGN PATENT DOCUMENTS

| | | | |
|---|---|---|---|
| 195639 | 9/1986 | European Pat. Off. | 358/84 |
| 284225 | 9/1988 | European Pat. Off. | 351/210 |

Primary Examiner—Keith E. George
Attorney, Agent, or Firm—Burns, Doane, Swecker & Mathis

[57] ABSTRACT

This invention discloses apparatus and methods for monitoring the television viewing acts of individuals by transmitting a signal toward the individual and detecting the reflection of the signal from the individual's eyes to determine the time intervals and total times the individual is viewing the television. This viewing information is then correlated with the program information from the television. The apparatus and method of this invention can be used to identify each individual viewing the television and track and correlate the viewing information for each individual. The signals reflected from each individual's eyes can also be used to determine changes in blink rate and/or pupil dilation in order to determine the emotional response of each individual to the program being viewed. This invention also provides a system for monitoring the times at which particular programs are viewed by particular individuals even when the individual records the program on a VCR and views the program at a later time.

20 Claims, 2 Drawing Sheets

APPARATUS AND METHODS FOR MONITORING TELEVISION VIEWERS

FIELD OF THE INVENTION

This invention is in the field of monitoring television viewers.

BACKGROUND OF THE INVENTION

The present invention generally relates to methods and apparatus for monitoring the viewers of a television. This invention in particular relates to a method and apparatus for accurately monitoring the actual viewing habits and activities of individuals viewing television programs without requiring any action on the part of the viewer.

Information about the viewing habits and activities of household members is very important to television networks and cable television companies. By determining the viewing time of various televised programs by individuals in selected households, the networks can determine the popularity of their shows. Such information is used by the networks to establish ratings for various programs or shows and to determine the advertising rates charged to sponsors who wish to air their televised commercials during those programs. Viewing information is also used by the advertising sponsors to determine the extent to which their commercials are being viewed by the television audience.

Several devices and systems have been described in the prior art for obtaining the desired information. Percy et al. in U.S. 4,646,145 describe a keyboard system for the television viewer to indicate not only that the viewer is watching a program, but also to indicate their preferences, reactions and ratings of the particular program being watched. The disadvantage of this system is that it requires direct viewer participation to record the necessary information and data through the viewer's keyboard.

Other systems have attempted to reduce the required participation by the television viewer while still being able to identify each individual viewer of the television program and recording the time which each viewer watcher the program in question. For example, Lurie, U.S. Pat. No. 4,626,904, Heller, U.S. Pat. No. 4,652,915 and Weinblatt, U.S. Pat. No. 4,695,879, each disclose systems involving headphones or a monitoring unit worn on the head of the individual watching the television program. These systems also suffer from the disadvantage that if the individual fails or forgets to wear the headphone or monitoring unit, then the desired information is not available. Some of these units attempted to make it essential for the individual to use the headphone unit, for example, by requiring the headphone unit to be in use on the individual before the audio portion of the television program is available to the individual. These systems have the disadvantage of being undesirable for the individual to use, since it is not always practical, comfortable or pleasant to watch television programs while wearing headphones or monitoring units on one's head. These systems can also give erroneous information if the headset is not oriented properly or is improperly worn by the individual, thus indicating that the individual is viewing the television when he or she actually is not or indicating they are not viewing when they actually are viewing the television.

Another system has been proposed which would obtain the desired information through a passive system, i.e., without any participation on the part of the television viewer. For example, Kiewit et al., U.S. Pat. No. 4,644,509, disclose an ultrasonic detection system for determining the number of people present in the area from which a television can be viewed. This system suffers from the disadvantage that it merely detects the presence of persons in the designated monitored area while the television is receiving a certain program; it does not indicate whether the persons present are actually watching the program. This system contains a desired feature that the system is passive with respect to the television viewer, i.e., there is no action required on the part of the viewer to activate the information collection system; however, this system collects incomplete and inadequate information and data regarding the actual viewing of the television programs.

It is apparent from the above that there exists a need for a television viewer monitoring device and system which is passive with respect to the television viewer and which collects and provides the desired accurate and detailed information regarding the television viewing activities of the individuals being monitored.

SUMMARY OF THE INVENTION

It is an object of the present invention to provide a novel apparatus, method and system for monitoring the television viewing activities of individuals. It is a further object of this invention to provide such apparatus, methods and systems which provide accurate and reliable information and data regarding the actual television viewing activities of an individual and which do not depend on any separate action or effort on behalf of the viewer for the completeness and accuracy of the information collected.

It is the further object of this invention to provide a system which will provide accurate and reliable information regarding the viewing of television programs through "time shift", i.e., by recording television programs on a video cassette recorder (VCR) and viewing the program at a later time.

This invention comprises apparatus for monitoring the television viewing acts of individuals comprising:

(a) means for transmitting a signal from the vicinity of a television;

(b) means for detecting reflections of a predetermined nature of said signals from the eyes of an individual in the viewing area of said television; and (c) means for determining whether the reflected signal, compared to predetermined criteria, indicates that the individual is viewing the television.

This invention further comprises a method for monitoring the television viewing acts of an individual comprising:

transmitting a signal from the vicinity of a television;

detecting reflections of said signal from the eyes of an individual in the viewing area of the television; and determining whether the reflected signal indicates that the individual is viewing the television.

In another aspect, this invention comprises apparatus for monitoring television viewing acts of an individual, wherein the television comprises a television-VCR combination, which comprises:

a monitor comprising means for collecting and storing data and means for placing a predetermined signal on a videotape when the VCR is recording a television program in the videotape;

means for detecting whether there is at least one person in the viewing area of the television when the television is operating and for transmitting that data to the monitor; and means for determining whether the program on the television is:
  (a) from a broadcast channel and for transmitting the channel information to the monitor; or
  (b) from the videotape previously recorded by the VCR and for transmitting to the monitor the information from the predetermined signal placed on the videotape by the monitor when the program was recorded.

In another aspect, this invention provides a method for monitoring the television viewing acts of an individual using a television-VCR combination which comprises:

placing a predetermined signal on a videotape when the VCR is recording a television program on the videotape;

detecting whether there is at least one person in the viewing area of the television when the television is operating; and determining whether the program on the television is (a) from a broadcast channel or (b) from the VCR by detecting the information from the predetermined signal placed on the videotape when the program was recorded by the VCR.

Numerous advantages of the above apparatus, methods and systems are explained herein and other advantages will become apparent to those skilled in the art from the following description of the embodiments of the invention as summarized herein and as defined by the claims appended hereto.

DESCRIPTION OF THE INVENTION

Figure 1:
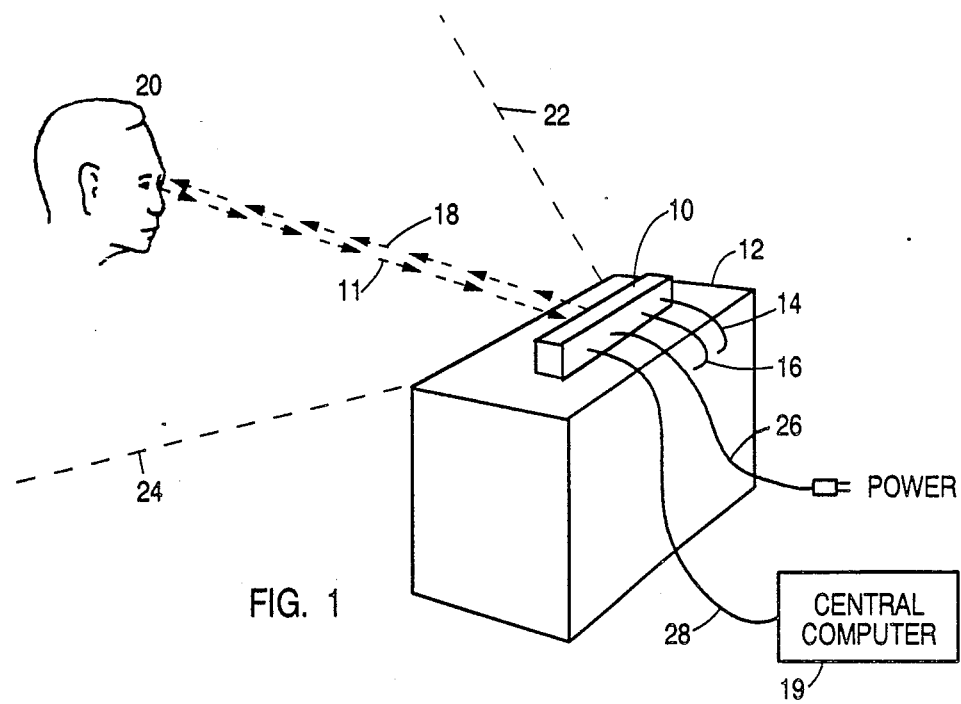
FIG. 1 is a general diagram of an embodiment of the present invention showing a monitor device for transmitting a signal which is reflected from the eyes of a television viewer and detected by the receiver in the device monitoring the television viewer.

FIG. 1 shows the basic components of one aspect of the present invention, which comprises a monitor unit 10, according to the present invention, in combination with television 12. Monitor unit 10 is connected to television 12 by cable means 14, which provides channel information from the tuner of television 12 to monitor 10. In addition, monitor 10 is connected to television 12 by cable means 16, which provides control means to activate monitor 10 when the television 12 is turned on. Monitor 10 contains transmitting means capable of transmitting a signal such as an infrared signal 18, which is adapted to be reflected by the eyes of viewer 20, whereby the reflected signal is received in a receiver means in monitor 10. Monitor 10 is capable of scanning and transmitting a signal and receiving a signal from the viewing area of the television, defined as being between lines 22 and 24. Monitor means 10 also includes power means 26 for an independent power supply to monitor 10 and communication line 28, which can be connected to a phone line to enable monitor 10 to communicate with a central computer for relaying information assembled by monitor 10 either at the time of viewing or at later time.

Figure 2:
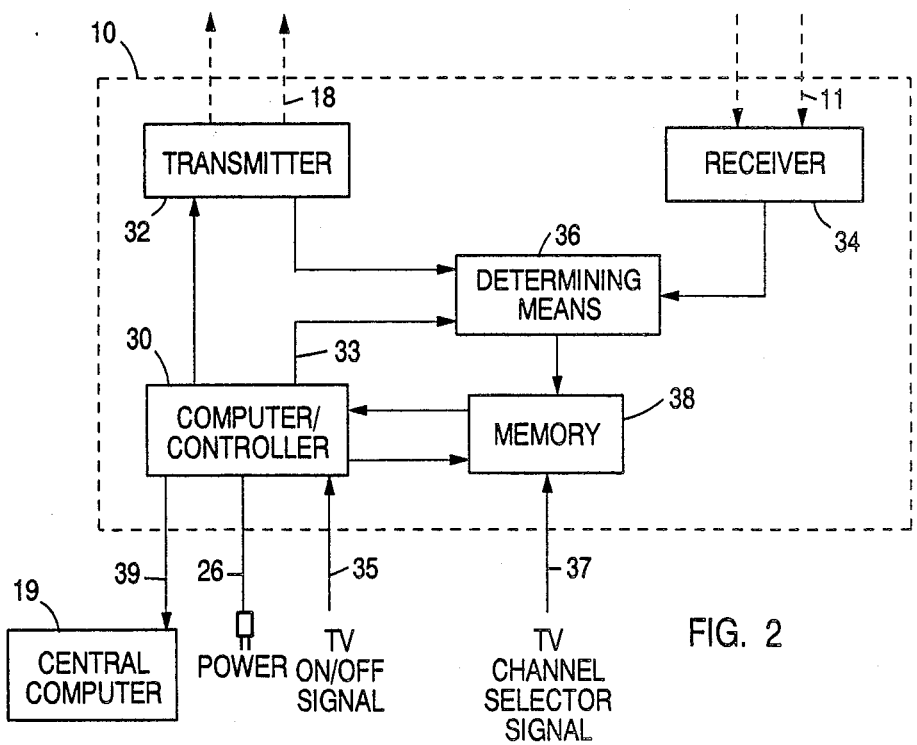
FIG. 2 is a schematic diagram of an embodiment of a monitor device shown in FIG. 1.

FIG. 2 is a schematic diagram of monitor 10, which illustrates that monitor 10 comprises a computer/controller 30 for controlling the other components in monitor 10. The computer/controller can be connected to the television by means 35 for an on/off signal to activate monitor 10 when the television is turned on. Transmitter 32 transmits a signal toward the viewers of the television, which is a signal that is adapted to be reflected from the eyes of the viewers in the viewing area of the television. Receiver 34 is adapted to receive and detect the signals reflected from the viewer's eyes and in combination with determining means 36, discriminates and filters the received reflections to determine which reflections are from the viewer's eyes and which reflections are from other objects. The signals determined to be reflections from the eyes of the viewers who are watching the television are transmitted to memory means 38, where the information is stored, along with the information from the television channel selector via means 37 regarding the program which is being watched.

Memory means 38 and computer/controller means 30 communicate to compile the desired information in the predetermined form. The computer and memory means preferably also contain clock means whereby viewer information received and processed through receiver 34, determining means 36 and the television channel selector information from means 37 can all be correlated with a clock time reference in memory 38 for future retrieval and use.

Computer means 30 can be connected to a central computer 19 via phone line 39 and can contain the appropriate modem and means whereby a signal through the phone line 39 from a central computer 19 or home office can activate the computer and retrieve the information stored in the memory 38 upon demand from the central computer without interfering with the operation of the monitor 10.

Computer/controller means 30 can also be connected to other components for appropriate control and/or interaction, such as to determining means 36 by means 33 and to receiver means 34 (by means not shown). In addition, each connection means can be two-way when desired for control and/or information, signal, data or sensing means transmission between the computer/controller means 30 and the other components in the system.

The various and numerous advantages of the present invention will be apparent from the operation of the invention as illustrated by the exemplary embodiments in FIGS. 1 and 2. One of the primary advantages is that the system is passive with respect to the television viewer. That is, the television viewer only needs to turn on the television set in order to activate the monitoring system of the present invention. The television viewer does not need to punch keyboards, wear headsets, keep logs or engage in any activity other than turning on the television set and watching the programs in the normal and conventional manner. The monitoring system of this invention provides far more reliable information than previous systems because of the absence of any requirement of activity, special equipment use or record keeping on the part of the television viewer.

Another advantage of the present invention is that the information provided by the apparatus and methods of the present invention is accurate, meaningful, detailed, diverse and complete, especially when compared to information provided by prior systems. The transmitter and receiver of the monitor of the present invention may be operated continuously to constantly monitor the persons watching the program which has been selected by the channel selector on the television set. By continuously monitoring the viewing area, the monitor of the present invention can determine the number of persons actually watching the program at any given time. In addition, the monitor, in combination with clock means, can precisely determine how much time and at what intervals each person is actually looking at the television set. In this regard, predetermined standards can be applied for particular programs to determine how much viewing time and at what intervals a person is actively viewing a television program or is engaged in some other activity without actually watching the program. By recording the viewing time and intervals of viewing, the monitor of the present invention can determine the level of interest in the program and/or what portion of the program was actually viewed by a particular viewer.

Another advantage of the monitor of the present invention is that the transmitter and receiver can be designed to transmit signals which can be reflected from the retina, iris and/or the cornea of the viewer's eyes or any combination thereof and the reflected signal analyzed to determine the unique characteristics of the reflected signal from each individual to thereby "fingerprint" each individual. The receiver determining means and memory in combination with the computer can continually track each individual to determine the viewing activities of each individual. In a preferred embodiment, it may be desirable that each individual in the household be "fingerprinted" and identified for the monitor's memory when the monitor is installed in the household. Such identity can be established by having each individual, in turn, monitored by the monitor of the invention for an initial period of time to establish the unique characteristics of the reflected signals from that individual's eyes. Then the individual can be identified by digital or keyboard input into the computer and/or memory, which identification can include information desired by the organization conducting the marketing information survey; for example, the viewers may be identified by number or name and/or can be identified by age, sex, household status, educational level, etc.

In addition to the above advantages, additional advantages can be realized by specific information monitoring. For example, by precise clock time correlation, the monitor device of this invention can determine which persons and how many persons view a commercial or any particular segment of a broadcast on any particular channel. In this way, broadcast networks or cable networks can monitor and determine the viewership of their programs, commercials, special announcements, news programs, or any other specific segment of their broadcast for which it is important to know the degree and level at which the viewers actually view that part of the broadcast programming.

In addition, the monitor of the present invention, by monitoring the actual eye positions and eye characteristics of each individual viewer can also determine additional information which may be of interest to the broadcast companies or advertisers. For example, changes in blink rate of each individual can be monitored, along with the changes in pupil dilation, which can be used as biofeedback variables to indicate the viewer's degree of interest in and emotional response to a particular segment of the broadcast programming.

Another advantage which is apparent from the present invention is that with the basic hardware components in place in the device for transmitting the appropriate signal, receiving the reflected signals and scanning the viewing area, the device can incorporate computer and memory hardware of appropriate size to enable installation of software to control and provide any degree of sophistication of and detail of the monitoring desired. In this way, the device can be controlled so that it functions to record and discriminate among any or all of the data which can be collected by the device of the present invention as outlined above. Through the computer/controller, the memory and modem combination in the device of the present invention, the accumulated information and data can then be accessed immediately by a phone line by a central office or computer or can be accumulated over a period of time and accessed periodically by the central office or computer.

Since the monitor device of the present invention requires no unusual action on the part of the viewer, such as record keeping or wearing a headset, it is believed that the actions of the viewer will be reflected as more natural, and the data will be more reliable than when the viewers are required to actively keep logs, wear equipment or type keyboard responses in order to accumulate the desired data.

It will be recognized that through the technology of high speed scanning, multiple signal transmitters and reservers and multiplexing of signals, the monitor of the present invention can be designed and programmed to continually scan the entire television viewing area for any number of individuals.

It will be recognized by those skilled in the art that the technology for detecting eye movement, eye position and detection of eye conditions such as blinking and pupil dilation is known in arts unrelated to television viewer monitoring. For example, see U.S. Pat. No. 3,507,988 to Holmes; U.S. Pat. No. 3,712,716 to Cornsweet et al.; U.S. Pat. No. 3,986,030 to Teltscher; U.S. Pat. No. 4,034,401 to Mann; U.S. Pat. No. 4,075,657 to Weinblatt et al.; U.S. Pat. No. 4,146,311 to Murr; and U.S. Pat. No. 4,582,403 and 4,623,230 to Weinblatt. The disclosures of these references are incorporated herein by reference.

In the present invention signals which can be used for reflections from the eye include light, preferably not in the visible range such as infrared; low-power UV or IR lasers which do not stress or damage the eyes; microwaves, such as used for motion detectors; sound, such as ultrasonics or combinations thereof. The light and laser signals will generally be preferred because they can operate through eyeglasses and give the desired reflected signals for detection. The signal or signals used can be adapted for reflection from the retina, iris, or cornea of the eye or any combination thereof in order to provide the desired reflected signals for determining eye position, blinks, pupil dialation, and the like.

The signals reflected from each viewer's eyes can be analyzed to determine the alignment of the eyes and compare that information with predetermined standards indicating whether the viewer is actually viewing the television or looking at other objects. The reflected signals can also be measured to determine and record the location of the viewer at various times in the viewing area, which may in turn be used in part to determine or verify the data indicating conditions most consistent with actual viewing of the television. In addition, the reflected signals can be used to measure and record the coordinates of the viewers eyes, which can aid in individual identity of each viewer and/or the head position of each viewer which may also be used to determine or verify data indicating conditions consistent with actually viewing the television.

Figure 3:
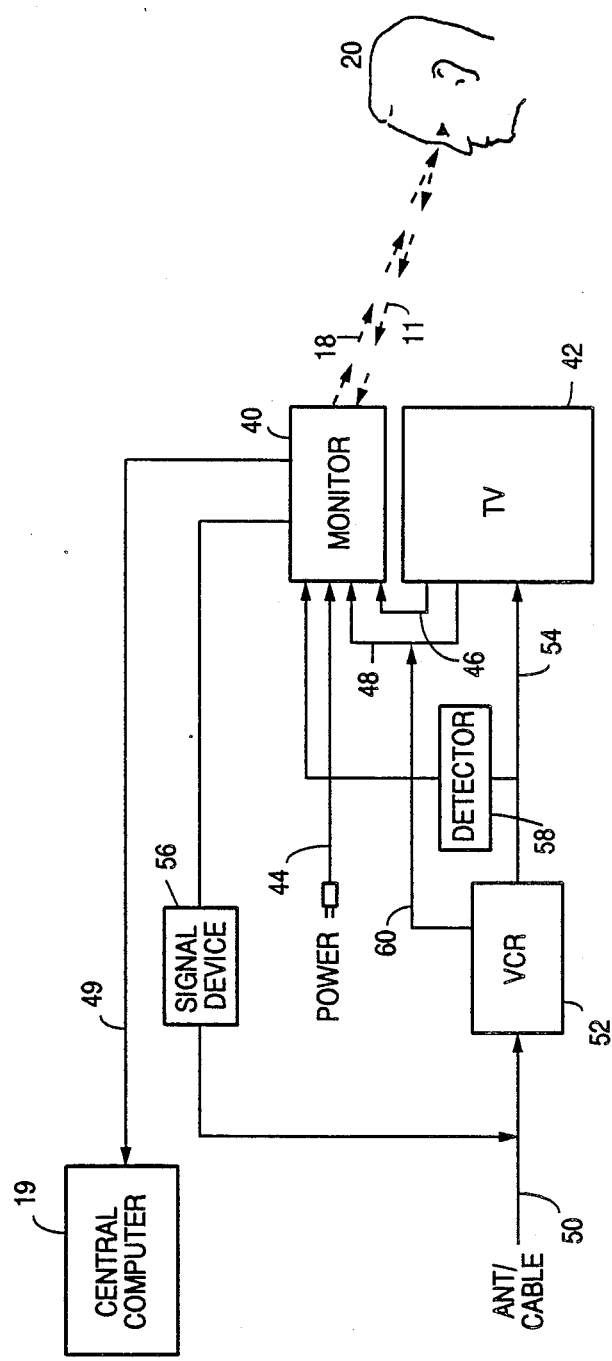
FIG. 3 is a schematic diagram of an embodiment of the aspect of this invention adapted for monitoring the viewing of broadcast programs recorded on a VCR.

In another aspect, this invention comprises apparatus, methods and systems for monitoring the actual viewing of broadcast and cable television programming, when viewed by individuals through "time shift" recording on video recorders, such as video cassette recorders (VCR's). It has become a common practice, due to work schedules and social schedules, to program timers on VCR's to record programs when the viewer is not available, and then the viewer watches the recorded program at the viewer's convenience. This "time shift" television viewing is of considerable interest to the programmers of broadcast and cable television networks. In particular, the programmers and their advertising sponsors are particularly interested in the degree to which the television viewers use time shift VCR viewing to skip over or fast forward through commercial messages. The device of the present invention provides means for monitoring the television viewer even on VCR time shift program viewing and obtaining and assembling information regarding the viewing habits or time shift viewers. In this aspect, the invention provides a device adapted for being placed in combination with the television and a VCR as shown in FIG. 3. In FIG. 3, monitor device 40, which has the same interconnect means with the television 42 as shown in FIGS. 1 and 2, namely, a power input means 44, means 46 from the television to the monitor to indicate when the television is on and to activate the monitor, and means 48, whereby the signal is transmitted from the television tuner to the monitor to indicate which channel the television is tuned to when the television is in operation. In addition to monitor 40, it can also include communication means 49, such as a modem and phone line to the central office or central computer 19, by which the information and data accumulated in and stored in the monitor 40 can be retrieved upon demand from the central office or central computer 19. Monitor means 40 also contains an appropriate means, such as the means described above for transmitting a signal and receiving the signal reflected from the eyes of the viewer for determining the presence of a viewer in the television viewing area when the television and the associated monitor is in operation. It should be noted that in this regard, the means for detecting and determining the presence of television viewers can be conventional means, but it is preferred that the above means for reflecting signals from the eyes of the viewers be used for the most accurate and meaningful information.

FIG. 3 also shows the conventional arrangement of the antenna or cable means 50 connected to VCR 52, which in turn is connected by means 54 to television 42. The monitor device of the present invention also includes signal means 56 for transmitting a signal into the VCR to be recorded on the videotape recording of a program which is recorded from the antenna or cable input 50. This predetermined signal from monitor 40 to VCR 52 via means 56 is a signal which does not interfere with the audio or visual portion of the recorded program, but is detectable by the monitor when the recorded program is played for viewing on TV. This predetermined signal from monitor 40 which has been recorded on the videotape when the program is recorded is detected by monitor 40 by detector means 58, which allows the video signal from VCR 52 being transmitted to television 42 by means 54 to be monitored by monitor 40 by means of input 50 from means 58.

As can be seen, if the predetermined signal transmitted by monitor 40 via signal means 56 into VCR 52 is simultaneously detected from means 54 via means 58, the monitor can easily determine that the program being received by the television is not from a previously recorded program, and in this mode the monitor 40 will record the viewing activities with respect to the broadcast programming being watched by the viewer, which is detected through means 48 from the television to monitor 40. If the VCR is on when the television is on, in most cases the channel received from means 50 from the antenna or cable is converted to a standard channel and transmitted to television 42 on means 54 on this standard channel. In this case, monitor 40 will need an additional input means 60 from the VCR to the monitor to inform the monitor with respect to whether the VCR is on or off and with respect to which incoming channel from the antenna or cable 50 is actually being transmitted to the television through means 54 and being viewed by the viewer.

When a recorded program is being played on the VCR for viewing on the television, the signal from the recorded tape is transmitted by means 54 to television 42. In this case, input means 58 between the VCR output and the monitor 40 will be detected by monitor 40 as a predetermined signal from a previously recorded program. The predetermined signal can be a periodic signal of time, date and channel for the program which was previously recorded on the VCR. In addition, the predetermined signal can include a timing means to determine the precise segments and portions of the prerecorded program which are being viewed when the program is played back on the VCR. In this mode of operation, the monitor 40 will then record the presence of viewers in the television viewing area, along with the program information for the previously recorded program and will record and analyze the actual viewing of the previously recorded program when it is played back. By having the predetermined signal recorded on the videotape containing the recorded program, the monitor can also determine, from the timing means contained in the predetermined signal recorded on the tape, the extent to which the viewer skips over or fast forwards through portions of the program, special announcements, commercial messages or other parts of the program which the programmers or sponsors want to determine whether the viewers actually watched. The monitor means 40 in this operation mode can also record the appropriate data to indicate the degree of time shift, i.e., the amount of time between recording the live program on the VCR and the time at which the television viewers actually watch the recorded program. In addition, the monitor means 40 can also determine from previously recorded data if the recorded program is watched more than once, and if the preferred viewer monitoring device described above with respect to transmitting and receiving signals reflected from the eyes of the viewers, the monitor device 40 can also determine whether the second and subsequent viewing of the recorded program is by the same or different viewers.

As explained above with respect to the other aspects of this invention, this aspect of the invention involving the television-VCR combination being monitored by the monitoring device of this invention, the hardware can be designed and installed so that the system can be controlled and driven by the software installed in the hardware. The software can then provide for any degree of sophistication of data and information desired and in any detail which is desired.

It will be appreciated by those skilled in the art that the present invention can be embodied in other specific forms without departing from the spirit or essential characteristics hereof. The presently disclosed embodiments are therefore considered in all respects to be illustrative and not restrictive. The scope of the present invention is indicated by the appended claims rather than the foregoing description of embodiments, and all changes that come within the meaning and range of equivalents thereof are intended to be embraced within the scope of the present invention. For example, some aspects of this invention are defined in terms of "videotape", "VCR" and/or "video recording means." It is to be clearly understood that in the description of this invention and in the appended claims such terms shall include equivalent means thereof, including any recording means that is optical, magnetic, thermal, etc., or that is on cassette tape, reel-to-reel tape, hard disk, floppy disk, digital memory, etc., so long as the predetermined signal from the monitor can be recorded along with the video program and used as described herein.

What is claimed is:

1. Apparatus for monitoring the television viewing acts of an individual comprising:
   means for transmitting a signal from the vicinity of a television into the viewing area of the television;
   means for detecting reflections of said signal from the eyes of an individual in the viewing area of the television; and
   means for determining whether the reflected signal satisfies predetermined criteria indicating that the individual is viewing the television.

2. Apparatus according to claim 1 further comprising means for recording the time intervals or total times the individual is viewing the television.

3. Apparatus according to claim 2 further comprising means for recording the identity of the television channel or television program and for correlating the time intervals or total times the television is viewed by the individual with the programs or part thereof viewed by the individual.

4. Apparatus according to claim 3 further comprising means for detecting reflections of the signal from the eyes of a plurality of individuals in the viewing area of the television and means for determining whether each individual is viewing the television.

5. Apparatus according to claim 3 further comprising means for communicating with a remote central office computer for transmitting the recorded information to the remote computer wherein the communication means is capable of activation upon demand by the central office computer.

6. A method for monitoring the television viewing acts of an individual comprising:
   transmitting a signal from the vicinity of a television into the viewing area of the television;
   detecting reflections of said signal form the eyes of an individual in the viewing area of the television; and
   determining wwhether the reflected signal indicates that the individual is viewing the television.

7. A method according to claim 6 further comprising recording the time intervals and total times that the individual is viewing the television.

8. A method according to claim 7 further comprising recording the identity of the channel or program and correlating the time intervals and total times with the programs or parts thereof viewed by the individual.

9. A method according to claim 8 further comprising carrying out said recording and correlating activities for a plurality of individuals.

10. A method according to claim 8 further comprising transmitting the recorded and correlated information to a central computer.

11. Apparatus for monitoring television viewing acts of an individual, wherein the television comprises a television-video recording means combination which comprises:
    a monitor comprising means for collecting and storing data and means for placing a predetermined signal on a video recording when the video recording means is recording a television program;
    means for detecting whether there is at least one person in the viewing area of the television when the television is operating and for transmitting that data to the monitor; and
    means for determining whether the program on the television is:
    (a) from a broadcast channel and for transmitting the channel information to the monitor; or
    (b) from the video recording previously recorded by the video recording means and for transmitting to the monitor the information from the predetermined signal placed on the video recording by the monitor when the program was recorded;
    wherein the means for detecting at least one person in the viewing area comprises means for transmitting a signal from the vicinity of the television into the viewing area of the television, means for detecting reflections of said signal from the eyes of the persons in the viewing area of the television and means for determining whether the 12. Apparatus according to claim 11 further comprising means for recording the time intervals or total times the individual is viewing the television.

13. Apparatus according to claim 12 further comprising means for recording the identity of the television channel or television program and for correlating the intervals or total times the television is viewed by the individual with the program or parts thereof viewed by the individual.

14. Apparatus according to claim 13 further comprising means for detecting reflections of the signals from the eyes of a plurality of individuals in the viewing area of the television and means for determining whether each individual is viewing the television.

15. Apparatus according to claim 13 further comprising means for communicating with remote central office computer for transmitting the recorded information to the remote computer wherein the communication means is capable of activation upon demand by the central office computer.

16. A method for monitoring the television viewing acts of an individual using a television-video recording means combination which comprises:

placing a predetermined signal on a video recording when the video recording means is recording a television program;

detecting whether there is at least one person in the viewing area of the television when the television is operating by transmitting a signal from the vicinity of the television into the viewing area, detecting reflections of the signal from the eyes of persons in the viewing area of the television and determining whether the reflected signal satisfies predetermined criteria indicating that each person is viewing the television; and determining whether the program on the television is (a) from a broadcast channel or (b) from the video recording means by detecting the information from the predetermined signal placed on the video recording when the program was recorded.

17. A method according to claim 16 comprising recording the time intervals and total times that the individual is viewing the television.

18. A method according to claim 17 comprising recording the identity of the channel on program and correlating the time intervals and total times with the programs or parts thereof viewed by the individual.

19. A method according to claim 18 comprising carrying out said recording and correlating activities for a plurality of individuals.

20. A method according to claim 18 comprising transmitting the recorded and correlated information to a central computer.

* * * * *